(12) United States Patent
Anderheggen et al.

(10) Patent No.: US 11,628,131 B2
(45) Date of Patent: Apr. 18, 2023

(54) AMMONIA-FREE BLEACHING KIT FOR GENTLE BRIGHTENING OF KERATINOUS FIBERS

(71) Applicant: Henkel AG & Co. KGaA, Duesseldorf (DE)

(72) Inventors: Bernd Anderheggen, Moenchengladbach (DE); Mechtild Grunwald, Langenfeld (DE); Oliver Nemitz, Duesseldorf (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 194 days.

(21) Appl. No.: 17/116,318

(22) Filed: Dec. 9, 2020

(65) Prior Publication Data

US 2021/0169762 A1   Jun. 10, 2021

(30) Foreign Application Priority Data

Dec. 9, 2019   (DE) .................... 10 2019 219 162.2

(51) Int. Cl.
| | |
|---|---|
| *A61Q 5/08* | (2006.01) |
| *A61K 8/46* | (2006.01) |
| *A61K 8/92* | (2006.01) |
| *A61K 8/34* | (2006.01) |
| *A61K 8/02* | (2006.01) |

(52) U.S. Cl.
CPC .............. *A61K 8/463* (2013.01); *A61K 8/022* (2013.01); *A61K 8/342* (2013.01); *A61K 8/92* (2013.01); *A61Q 5/08* (2013.01); *A61K 2800/30* (2013.01); *A61K 2800/59* (2013.01)

(58) Field of Classification Search
CPC ........ A61Q 5/08; A61K 8/22; A61K 2800/88; A61K 2800/882; A61K 8/342; A61K 2800/31; A61K 2800/59; A61K 2800/30; A61K 8/92; A61K 8/022; A61K 8/463

USPC ........................................................... 424/62
See application file for complete search history.

(56) References Cited

U.S. PATENT DOCUMENTS

| | | | | |
|---|---|---|---|---|
| 11,033,477 | B2 * | 6/2021 | Anderheggen | A61K 8/31 |
| 2011/0311465 | A1 * | 12/2011 | Burg | A61Q 5/04 |
| | | | | 206/223 |
| 2013/0269721 | A1 | 10/2013 | Gross et al. | |
| 2014/0158150 | A1 * | 6/2014 | Schoepgens | A61K 8/22 |
| | | | | 424/62 |
| 2014/0283866 | A1 * | 9/2014 | Schmahl | A61Q 5/08 |
| | | | | 132/286 |
| 2017/0340549 | A1 * | 11/2017 | Anderheggen | A61K 8/24 |
| 2017/0340553 | A1 * | 11/2017 | Anderheggen | A61K 8/922 |
| 2018/0008524 | A1 * | 1/2018 | Anderheggen | A61K 8/23 |
| 2019/0175462 | A1 * | 6/2019 | Hodes | A61K 8/19 |
| 2020/0206104 | A1 * | 7/2020 | Erkens | A61K 8/19 |
| 2021/0277182 | A1 * | 9/2021 | Hodes | A61K 8/88 |
| 2021/0283026 | A1 * | 9/2021 | Nowottny | B32B 1/08 |

FOREIGN PATENT DOCUMENTS

| | | |
|---|---|---|
| DE | 102008036952 A1 | 6/2009 |
| WO | 2007068307 A1 | 6/2007 |

* cited by examiner

*Primary Examiner* — Eisa B Elhilo
(74) *Attorney, Agent, or Firm* — Lorenz & Kopf, LLP

(57) ABSTRACT

The object of the present disclosure is a three-component kit for brightening keratinous fibers, in particular human hair, comprising a blonding powder for mild blonding of keratinous fibers with as natural ingredients as possible, containing at least one oxidizing agent, selected from the group of sodium salts and potassium salts of a peroxosulfuric acid, an oil mixture of at least one branched fatty alcohol having 8-24 carbon atoms, and at least one dialkyl ether having 6-18 carbon atoms in the alkyl group, in which no ammonium compounds, no paraffin oil, no mineral oil and no silicone compounds being present in the blonding powder.

20 Claims, No Drawings

AMMONIA-FREE BLEACHING KIT FOR GENTLE BRIGHTENING OF KERATINOUS FIBERS

CROSS-REFERENCE TO RELATED APPLICATION

This application claims priority to German Patent Application No. 10 2019 219 162.2, filed Dec. 9, 2019, which is incorporated herein by reference in its entirety.

TECHNICAL FIELD

The present disclosure concerns bleaching powders used as part of a three-component kit for lightening or brightening keratinous fibers, such as human hair. Furthermore, the present disclosure relates to the use of the agents for gentle bleaching or oxidative brightening of human hair as well as a kit-of-parts for brightening keratinous fibers, which comprises a bleaching powder and separately therefrom an oxidizing composition and an alkalizing composition.

Furthermore, a process for the oxidative brightening of keratinous fibers using the said bleaching powder and the kit comprising this bleaching powder is described.

BACKGROUND

The blonding powder is an anhydrous, powdered oxidizing agent preparation containing at least one persalt.

Lightening one's own hair color has always been the wish of many consumers, as a blonde hair color is considered attractive and desirable in terms of fashion. For this purpose, various bleaching agents with different bleaching power are available on the market. The oxidants contained in these products can lighten the hair fiber by oxidative destruction of the hair's own dye melanin. For a moderate bleaching effect, the use of hydrogen peroxide—possibly with the addition of ammonia or other alkalizing agents—as oxidizing agent alone is sufficient. A mixture of hydrogen peroxide and at least one compound selected from persalts, especially peroxodisulfate salts and/or peroxomonosulfate salts, is usually used to achieve a stronger bleaching effect. To enhance the blonding effect, the agents contain higher concentrations of hydrogen peroxide and persalts, especially persulfates. Dark, dark brown or black hair can be lightened by 4 to 6 shades in one step. The hydrogen peroxide and the persalts are stored separately until use in order not to deactivate the persalts prematurely. The hydrogen peroxide component, which comprises an aqueous solution of hydrogen peroxide, has an acidic pH, especially a pH of 1.5 to 5.5, especially 3 to 5, measured at 20° C. to stabilize the hydrogen peroxide.

However, for the melanin-degrading effect of the hydrogen peroxide and the blonding effect on the keratinous fiber, it is advantageous if the application mixture of hydrogen peroxide solution and persalt has an alkaline pH value, preferably in the range of 8 to 12, particularly preferably in the range of 8.5 to 11.5, extremely preferably in the range of 9 to 10.5, measured at 20° C.

There are several possibilities to adjust an alkaline pH-value of the brightening application mixture:

In addition to at least one persalt, the bleaching powder contains at least one powdered alkalizing agent in such a total amount that the application mixture has the desired alkaline pH value: or the hydrogen peroxide solution is not only combined with the blonding powder, but additionally with an alkalizing agent preparation for the application mixture If oxidation dye precursors and/or direct dyes are added to the alkalizing agent preparation and/or the blonding powder, the hair can be dyed simultaneously. Appropriate 3-component hair dyes are offered especially for consumers with very dark hair rich in melanin.

For safety reasons, the blonding powders should be formulated in such a way that they do not produce, or only produce as little dust as possible during use, especially before or during mixing with the liquid hydrogen peroxide solution and, if necessary, the alkalizing agent preparation. Suitable features for reducing dust are in particular oils which are mixed with the dust-creating components of the blonding powder, the total amount of oils being from about 0.2-20% by weight, based on the weight of the dusted blonding powder. The application properties of the bleaching powder as well as of the entire ready-to-use bleaching agent can be optimized by skillful selection of the oils. The choice of oils should also take into account the consumer's desire for products that contain as few synthetically produced ingredients as possible, but rather naturally derived ingredients, while also avoiding as far as possible ingredients of mineral origin, such as mineral oils and paraffins.

A further requirement for the blonding powder as contemplated herein was to allow blonding that is as mild as possible Ammonium hydroxide and ammonium salts have therefore been omitted because they can release ammonia in the strongly alkaline medium of the application preparation, which could irritate the scalp and mucous membranes of the user. A further requirement for the blonding powder as contemplated herein was to avoid completely synthetic ingredients as far as possible when selecting the inert carrier components, in particular synthetic ingredients on a petrochemical basis, such as polyacrylates. In contrast, natural ingredients should be preferred, whereby the characteristic "natural" also includes chemical and/or physical modifications of a natural ingredient. Examples are cellulose as a natural polysaccharide and hydroxyethyl cellulose and carboxymethyl celluloses as chemical derivatives of natural cellulose, which are also considered "natural" ingredients for the purposes of this notification.

BRIEF SUMMARY

Kits-of-parts and methods for brightening keratinous fibers are provided. In an exemplary embodiment, a kit-of-arts includes three separately packaged components. The first component is a blonding powder (B) including a) an oxidizing agent selected from the group of sodium salts of a peroxosulfuric acid and/or potassium salts of the peroxosulfuric acid. The blonding powder (B) also includes b) from about 0.1 to about 15% by weight of at least one branched fatty alcohol with 8-24 carbon atoms, c) from about 0.1 to about 15% by weight of at least one dialkyl ether with 6 to 18 C atoms in the alkyl group, and d) from about 0 to about 8% by weight of water, based on the weight of the blonding powder. The total amount of oils, which includes components b) and c), is from about 0.2 to about 20% by weight, based on the weight of the blonding powder (B). The blonding powder (B) does not include ammonium compounds, paraffin oil, mineral oil, or silicone compounds. The second component is an oxidizing composition (OX) that includes from about 50 to about 90% by weight of water, and from about 0.5 to about 20% by weight of hydrogen peroxide, based on a weight of the oxidizing composition (OX). The oxidizing composition (OX) has a pH in the range of from about 1.5 to about 5.5, measured at about 20° C. The third component is an alkalizing composition (Alk) that is free from ammonia and ammonium salts. The alkalizing composition (Alk) includes water and an alkalizing agent selected from the group of alkanolamines, basic amino acids, alkali hydroxides, and mixtures thereof. The alkalizing composition (Alk) has a pH in the range of from about 8 to about 12, measured at about 20° C. The blonding powder (B), the oxidizing composition (Ox), and the alkalizing composition (Alk) are present in a weight ratio (B):(Ox):(Alk) of from (0.7-1.3):(2-3):(2-3).

In another embodiment, a method for brightening keratinous fibers is provided. The method includes mixing a blonding powder (B) with an oxidizing composition (Ox) and an alkalizing composition (Alk) to form an application mixture. The blonding power (B) includes a) an oxidizing agent selected from the group of sodium salts of a peroxosulfuric acid and/or potassium salts of the peroxosulfuric acid. The blonding powder (B) also includes b) from about 0.1 to about 15% by weight of at least one branched fatty alcohol with 8-24 carbon atoms, c) from about 0.1 to about 15% by weight of at least one dialkyl ether with 6 to 18 C atoms in the alkyl group, and d) from about 0 to about 8% by weight of water, based on the weight of the blonding powder. The total amount of oils, which includes components b) and c), is from about 0.2 to about 20% by weight, based on the weight of the blonding powder (B). The blonding powder (B) does not include ammonium compounds, paraffin oil, mineral oil, or silicone compounds. The oxidizing composition (OX) includes from about 50 to about 90% by weight of water, and from about 0.5 to about 20% by weight of hydrogen peroxide, based on a weight of the oxidizing composition (OX). The oxidizing composition (OX) further includes a pH adjusting agent in an amount to provide the oxidizing composition (OX) with a pH in the range of from about 1.5 to about 5.5, measured at about 20° C. The alkalizing composition (Alk) is free from ammonia and ammonium salts, and includes water and an alkalizing agent selected from the group of alkanolamines, basic amino acids, alkali hydroxides, and mixtures thereof. The alkalizing composition (Alk) has a pH in the range of from about 8 to about 12, measured at about 20° C. The application mixture is applied to the keratin-containing fibers, and left on the keratin-containing fibers for from about 5 to about 60 minutes. The keratin-containing fibers are rinsed with water, and optionally washed with a surfactant-containing detergent. The blonding powder (B), the oxidizing composition (Ox), and the alkalizing composition (Alk) are present in the application mixture in a weight ratio (B):(Ox):(Alk) of (0.7-1.3):(2-3):(2-3).

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, these tasks were solved by the object of the claims. As contemplated herein, keratin or keratinous fibers are defined as furs, wool, feathers, and especially human hair. Although the agents as contemplated herein are primarily suitable for bleaching and/or lightening fibers containing keratin, there is nothing in principle to prevent their use in other areas.

A first object of the present disclosure is a kit-of-parts for brightening keratinous fibers, such as human hair, containing at least three separately packaged components:

i) the first component (B) is a blonding powder containing
a) at least one oxidizing agent selected from the sodium salts and potassium salts of a peroxosulfuric acid, and mixtures thereof,
b) furthermore from about 0.1-15% by weight of at least one branched fatty alcohol with 8-24 carbon atoms, each based on the weight of the blonding powder,
c) furthermore from about 0.1-15% by weight of at least one dialkyl ether with 6 to 18 C atoms in the alkyl group, in each case based on the weight of the blonding powder,
d) and from about 0 to 8% by weight, preferably from about 0.1 to 5% by weight, particularly preferably from about 0.5 to 3% by weight of water, in each case based on the weight of the blonding powder,
e) wherein the total amount of oils, including components b) and c), is from about 0.2-20% by weight, based on the weight of the blonding powder, and
f) wherein the blonding powder does not contain ammonium compounds, paraffin oil, mineral oil, or silicone compounds,
ii) the second component is an oxidation composition (Ox) containing, in each case based on its weight, from about 50-96%, preferably from about 70-93%, more preferably from about 80-90%, by weight of water and from about 0.5-20% by weight of hydrogen peroxide and having a pH in the range of from about 1.5 to about 5.5, measured at 20° C.,
iii) the third component is an alkalizing composition (Alk) which is free from ammonia and ammonium salts and which contains water and at least one alkalizing agent selected from alkanolamines, basic amino acids and alkali hydroxides and mixtures thereof and has a pH in the range of from about 8-12, preferably from about 9-11, particularly preferably from about 9.5-10.5, each measured at about 20° C., the blonding powder (B), the oxidizing composition (Ox) and the alkalizing composition (Alk) being present in a weight ratio (B):(Ox):(Alk) from (0.7-1.3):(2-3):(2-3), particularly preferred (0.8-1.2):(2.3-3):(2.3-3), exceptionally preferred 1:2.5:2.5 or 1:3:3, to each other.

As contemplated herein, the term "powder" or "powdery" means a solid, free-flowing dosage form including individual particles, solid at about 20° C. and about 1013 mbar, in which the individual particles have particle sizes ranging from about 0.1 µm to a maximum of about 1.6 mm. The particle size distribution can preferably be determined by laser diffraction measurement according to ISO 13320-1 (2009). If necessary, the particle size of the blonding powder can be adjusted by physical treatment, such as sieving, pressing, granulating or pelletizing, or by the addition of certain auxiliary substances, to meet the requirements of the blonding powder, e.g. to improve the miscibility of the individual powder components or the miscibility of the blonding powder with a hydrogen peroxide preparation.

Blonding powders preferred according to the present disclosure have a bulk density in the range of from about 400 to about 1000 g/l (grams/liter), preferably from about 450 to about 900 g/l, especially preferred from about 550 to about 820 g/l. The bulk density is preferably determined according to EN ISO 60 (version January 2000) or DIN ISO 697 (version January 1984).

Unless otherwise stated, all temperature specifications refer to a pressure of about 1013 mbar.

The term "ammonium salt" refers to salts with the cation $NH_4^+$ and an anionic counter ion. Quaternary ammonium compounds in which one or more H atoms on the nitrogen atom are replaced by an organic group, e.g. an alkyl group, in particular tetraalkylammonium-based surfactants, are not covered by the term "ammonium salt".

The blonding powder as contemplated herein contains as the first essential component at least one oxidizing agent selected from inorganic salts of a peroxosulfuric acid and mixtures thereof.

Peroxosulfuric acids are peroxodisulfuric acid and peroxomonosulfuric acid (Caro's acid).

The oxidizing agent preferably includes at least one inorganic salt of peroxosulfuric acid selected from alkali metal peroxodisulfates, alkali metal peroxomonosulfates and alkali metal hydrogen peroxomonosulfates. Potassium peroxodisulfate, sodium peroxodisulfate and potassium hydrogen peroxomonosulfate are particularly preferred. Furthermore, during the work on the present disclosure, it has proved to be particularly preferred if the blonding powder as contemplated herein contains at least two different peroxodisulfates. Preferred peroxodisulfate salts are mixtures of potassium peroxodisulfate and sodium peroxodisulfate.

Preferred blonding powders as contemplated herein contain at least one oxidizing agent selected from inorganic salts of a peroxosulfuric acid and mixtures thereof in a total amount of from about 5-85% by weight, preferably from about 10-70% by weight, particularly preferably from about 17-55% by weight, extremely preferably from about 22-45% by weight, in each case based on the weight of the blonding powder.

The blonding powder of the blonding kit as contemplated herein contains as a second essential constituent from about 0.1-15% by weight of at least one branched fatty alcohol with 8-24 carbon atoms, each based on the weight of the blonding powder, as oil component b). The branched alcohols are often referred to as Guerbet alcohols because they are obtained by the Guerbet reaction. Preferred branched fatty alcohols with 8-24 carbon atoms are selected from 2-octyldodecanol, 2-hexyldecanol, 2-ethylhexyl alcohol and isostearyl alcohol and mixtures thereof. As contemplated herein, 2-octyldodecanol is extremely preferred as oil component b). The at least one branched fatty alcohol with 8-24 carbon atoms is contained in a total amount of from about 0.1-15% by weight, preferably from about 1-13% by weight, particularly preferably from about 5-12% by weight, each based on the weight of the blonding powder. Extraordinarily preferred blonding powders are exemplified by a content of from about 0.1-15% by weight, preferably from about 1-13% by weight, particularly preferably from about 5-12% by weight, of 2-octyldodecanol, in each case based on the weight of the blonding powder.

The blonding powder as contemplated herein contains as a third essential constituent from about 0.1-15% by weight of at least one dialkyl ether with 6 to 18 C atoms in the alkyl group, based on the weight of the blonding powder, as oil component c).

As oil component c) particularly preferred dialkyl ethers are di-n-alkyl ethers with a total of 12 to 36 C atoms, especially 16 to 24 C atoms in the molecule, such as di-n-octyl ether, di-n-decyl ether, di-n-nonyl ether, di-n-undecyl ether, di-n-dodecyl ether, di-n-octadecyl ether, n-hexyl-n-octyl ether, n-octyl-n-decyl ether, n-decyl-n-undecyl ether, n-undecyl-n-dodecyl ether and n-hexyl-n-undecyl ether. Also preferred dialkyl ethers are those with branched alkyl groups each with 6 to 18 C atoms, especially with alkyl groups substituted in the 2-position with an ethyl group. Preferred branched-chain dialkyl ethers with 6 to 18 C atoms in the alkyl group are selected from di-(2-ethylhexyl)ether and di-(2-ethyldecyl)ether.

Di-n-octyl ether is highly preferred (INCI: Dicaprylyl ether), which is commercially available for example under the name Cetiol® OE The at least one dialkyl ether with 6 to 18 C atoms in the alkyl group is contained in a total amount of from about 0.1-15% by weight, preferably from about 0.5-10% by weight, particularly preferably from about 1-5% by weight, extremely preferably from about 2-3% by weight, each based on the weight of the blonding powder. Extraordinarily preferred blonding powders are exemplified by a content of from about 0.1-15% by weight, preferably from about 0.5-10% by weight, particularly preferably from about 1-5% by weight, extremely preferably from about 2-3% by weight of di-n-octyl ether, in each case based on the weight of the blonding powder.

In blonding powders, the weight ratio of the total amount of branched fatty alcohols with 8-24 carbon atoms to the total amount of dialkyl ethers with 6 to 18 carbon atoms in the alkyl group is 2-8, preferably 3-6. The weight ratio of 2-octyldodecanol to di-n-octyl ether is 2-8, preferably 3-6, in blonding powders which are used with extraordinary preference.

The total amount of oils, including components b) and c), is from about 0.2-20% by weight, preferably from about 1-17% by weight, particularly preferably from about 3-16% by weight, extremely preferably from about 5-15% by weight, further extremely preferably from about 9-14% by weight, each based on the weight of the blonding powder.

The blonding powders of the kit as contemplated herein are anhydrous, which in the sense of the present disclosure means that they contain from about 0 to 8% by weight, preferably from about 0.1 to 5% by weight, particularly preferably from about 0.5 to 3% by weight of water, each based on the weight of the blonding powder.

These figures refer to the content of free water. Not considered is the content of molecularly bound water or water of crystallization, which individual powder components may have. The water content can be determined by Karl Fischer titration according to ISO 4317 (Version 2011-12).

The blonding powders of the kit as contemplated herein are further exemplified by the fact that they do not contain ammonium compounds, paraffin oil, mineral oil, or silicone compounds.

In addition to the mandatory oil components b) and c), the blonding powder as contemplated herein may contain at least one additional oil, provided that the total amount of oils, including components b) and c), is in the range of from about 0.2-20% by weight, based on the weight of the blonding powder, and the additional oil is not a paraffin oil, mineral oil or silicone compound.

In addition to the oil components b) and c), the blonding powders of the blonding kits as contemplated herein may optionally contain a further oil which is not a paraffin oil, a mineral oil or a silicone compound, wherein the total amount of oils, including components b) and c), is in the range of from about 0.2-20% by weight, based on the weight of the blonding powder. Preferably, the total amount of optional oils is from about 0.05-5% by weight, particularly preferably from about 0.1-3% by weight, extremely preferably from about 0.2-1% by weight, each based on the weight of the blonding powder.

As contemplated herein, preferred optional oils are selected from the benzoic acid esters of linear or branched C8-22 alkanols. Benzoic acid C12-C15 alkyl esters are particularly preferred.

Other optional oils preferred by the present disclosure are selected from the triglycerides (=triple esters of glycerol) of linear or branched, saturated or unsaturated, optionally hydroxylated C8-30 fatty acids. Natural oils include, e.g.

Amaranth seed oil, apricot kernel oil, argan oil, avocado oil, babassu oil, cotton seed oil, borage seed oil, camelina oil, thistle oil, peanut oil, pomegranate kernel oil, grapefruit seed oil, hemp oil, hazelnut oil, elderberry seed oil, currant seed oil, jojoba oil, linseed oil, macadamia nut oil, corn germ oil, almond oil, marula oil, Evening primrose oil, olive oil, palm oil, palm kernel oil, Brazil nut oil, pecan oil, peach kernel oil, rapeseed oil, castor oil, sea buckthorn pulp oil, sea buckthorn seed oil, sesame oil, soybean oil, sunflower oil, grape seed oil, walnut oil, wild rose oil, wheat germ oil, and the liquid portions of coconut oil and the like. Preferred are saturated triglyceride oils, especially Capric/Caprylic Triglycerides.

Other optional oils which are particularly preferred as contemplated herein are selected from the dicarboxylic acid esters of linear or branched C2-C10 alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Other optional oils which are particularly preferred by the present disclosure are selected from the esters of linear or branched saturated or unsaturated fatty alcohols with 2-30 carbon atoms with linear or branched saturated or unsaturated fatty acids with 2-30 carbon atoms, which may be hydroxylated. These are preferably 2-hexyl decyl stearate, 2-hexyl decyl laurate, isodecyl neopentanoate, isononyl isononanoate, 2-ethylhexyl palmitate and 2-ethylhexyl stearate, Isopropyl myristate, isopropyl palmitate, isopropyl stearate, isopropyl isostearate, isopropyl oleate, isooctyl stearate, isononyl stearate, isocetylstearate, isononylisononanoate, isotridecylisononanoate, cetearylisononanoate, 2-ethylhexyl laurate, 2-ethylhexyl isostearate, 2-ethylhexyl cocoate, 2-octyldodecyl palmitate, butyloctanoic acid 2-butyloctanoate, diisotridecyl acetate, n-butyl stearate, n-hexyl laurate, n-decyl oleate, oleyl oleate, oleylerucate, erucyl oleate, erucylerucate, ethylene glycol dioleate and ethylene glycol dipalmitate.

Other optional oils preferred by the present disclosure are selected from the $C_8$-$C_{22}$ fatty alcohol esters of monovalent or polyvalent $C_2$-$C_7$ hydroxycarboxylic acids, especially the esters of glycolic acid, lactic acid, malic acid, tartaric acid, citric acid and salicylic acid, e.g. $C_{12}$-$C_{15}$ alkyl lactate.

Other optional oils preferred by the present disclosure are selected from the symmetrical, asymmetrical or cyclic esters of carbonic acid with $C_{3-22}$ alkanols, $C_{3-22}$ alkane diols or $C_{3-22}$ alkane triols, e.g. dicaprylylcarbonate, or the esters according to DE19756454 A1, especially glycerin carbonate.

Preferred blonding powders as contemplated herein may include an optional oil that is selected from the benzoic acid esters of linear or branched $C_{8-22}$ alkanols; triglycerides of linear or branched, saturated or unsaturated, optionally hydroxylated $C_{8-30}$ fatty acids, especially natural oils; the dicarboxylic acid esters of linear or branched $C_2$-$C_{10}$ alkanols; the esters of linear or branched saturated or unsaturated fatty alcohols containing 2-30 carbon atoms with linear or branched saturated or unsaturated fatty acids containing 2-30 carbon atoms, which may be hydroxylated; the $C_8$-$C_{22}$ fatty alcohol esters of monovalent or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanediols; the esters of dimers of unsaturated $C_{12}$-$C_{22}$ fatty acids (dimer fatty acids) with monovalent linear, branched or cyclic $C_2$-$C_{18}$ alkanols or with polyvalent linear or branched $C_2$-$C_6$ alkanols, and mixtures of the above substances.

A blonding powder preferred as contemplated herein still contains hydroxyethyl cellulose (INCI) quaternized with diallyldimethylammonium chloride as an optional component. Polyquaternium-4 is particularly preferably contained in a total amount of from about 0.010-0.500 wt. %, particularly preferably from about 0.050-0.300 wt. %, further particularly preferably from about 0.090-0.200, extremely preferably from about 0.095-0.150 wt. %, each based on the weight of the blonding powder.

Another blonding powder preferred as contemplated herein also contains 2-[2-hydroxy-3-(trimethylammonio) propoxy]ethyl cellulose ether chloride (INCI) as an optional component: polyquaternium-10). The 2-[2-hydroxy-3-(trimethylammonio)propoxy]ethyl cellulose ether chloride is particularly preferably contained in a total amount of from about 0.01-1.00% by weight, particularly preferably from about 0.10-0.60% by weight, further particularly preferably from about 0.20-0.48, extremely preferably from about 0.30-0.47% by weight, in each case based on the weight of the blonding powder.

A further blonding powder preferred as contemplated herein further contains as an optional component at least one amino acid selected from arginine, lysine, histidine or at least one of the salts of these amino acids. Arginine is highly preferred. As contemplated herein, mixtures of arginine and lysine may be particularly preferred. Among the salts of arginine, lysine or histidine preferred by the present disclosure are the alkali metal salts and alkaline earth metal salts, in particular the salts of lithium, sodium, potassium, magnesium and calcium, as well as hydrohalides, in particular hydrochlorides, and mixtures of these salts. As contemplated herein, lysine hydrochloride is a particularly preferred amino acid salt.

As contemplated herein, particularly preferred amino acid mixtures are selected from arginine/lysine hydrochloride and arginine/lysine.

The amino acids, selected from arginine, lysine, histidine, and their salts as contemplated herein, may also contain water of crystallization.

Blonding powders of extraordinary preference as contemplated herein contain at least one amino acid selected from arginine, lysine, histidine or at least one salt of these amino acids in a total amount, converted to the mass of free amino acid, of from about 0.1-7% by weight, preferably from about 0.2-5% by weight, particularly preferably from about 0.5-2.5% by weight, extremely preferably from about 1-2% by weight, in each case based on the weight of the blonding powder.

Blonding powders preferred as contemplated herein contain at least one inorganic alkalizing agent solid at about 20° C. and 1013 mbar, preferably in a total amount of from about 4-70% by weight, preferably from about 10-65% by weight, particularly preferably from about 15-60% by weight, extremely preferably from about 20-55% by weight, in each case based on the weight of the blonding powder.

Blonding powders preferred as contemplated herein additionally contain at least one inorganic alkalizing agent solid at about 20° C. and 1013 mbar, including at least one sodium silicate or sodium metasilicate with a molar $SiO_2/Na_2O$ ratio of ≥2, preferably from about 2.5-3.5, in a total amount of from about 0.1 to about 50% by weight, preferably from about 4 to about 30% by weight, particularly preferably from about 15-25% by weight, in each case based on the weight of the blonding powder.

In addition to the at least one sodium silicate or sodium metasilicate with a molar $SiO_2/Na_2O$ ratio of $\geq 2$, preferably from about 2.5-3.5, in a total amount of from about 0.1-50 wt. %, preferably from about 4-30 wt. %, particularly preferably from about 15-25 wt.-%, in each case based on the weight of the blonding powder, as optional alkalizing agents that may be further included are inorganic alkalizing agents selected from alkaline earth metal silicates, which are solid at about 20° C. and 1013 mbar and are particularly preferred as contemplated herein, alkaline earth metal hydroxide carbonates, alkaline earth metal carbonates, alkaline earth metal metasilicates, alkali metal hydroxides, alkaline earth metal hydroxides, (earth) alkali metal phosphates and (earth) alkali metal hydrogen phosphates and mixtures of these substances. As contemplated herein, particularly preferred inorganic alkalizing agents which are solid at about 20° C. and 1013 mbar are, in addition to the at least one obligatory sodium silicate or sodium metasilicate, each with a molar $SiO_2/Na_2O$ ratio of $\geq 2$, preferably from about 2.5 to about 3.5, selected from magnesium hydroxide carbonates and mixtures of these alkalizing agents. As contemplated herein, preferred magnesium hydroxide carbonates are those with the formula $MgCO_3 \cdot Mg(OH)_2 \cdot 2H_2O$ and those with the formula $MgCO_3 \cdot Mg(OH)_2$. Magnesium hydroxide carbonate with the formula $MgCO_3 \cdot Mg(OH)_2$ is particularly preferred as contemplated herein.

Blonding powders particularly preferred as contemplated herein contain, in each case based on their total weight, from about 0.1 to 50% by weight, preferably from about 4-30% by weight, particularly preferably from about 15-25% by weight, of sodium silicates with a molar $SiO_2/Na_2O$ ratio of $\geq 2$, preferably from about 2.5 to about 3.5, and from about 2-40% by weight, preferably from about 5-35% by weight, particularly preferably from about 10-32% by weight, of magnesium hydroxide carbonate as inorganic alkalizing agents solid at about 20° C. and 1013 mbar.

Blonding powders of extraordinary preference as contemplated herein contain, in each case based on their total weight, from about 0.1 to about 50 wt. %, preferably from about 4-30 wt. %, particularly preferably from about 15-25 wt. %, sodium silicates with a molar $SiO_2/Na_2O$ ratio of $\geq 2$, preferably from about 2.5 to about 3.5, and from about 2-40 wt. %, preferably from about 2.5 to about 3.5. %, preferably from about 5-35% by weight, particularly preferably from about 10-32% by weight, of magnesium hydroxide carbonate having the formula $MgCO_3 \cdot Mg(OH)_2$ as inorganic alkalizing agents solid at about 20° C. and 1013 mbar.

In a preferred form, the blonding powder of the kit as contemplated herein further contains at least one dicarboxylic acid with 2 to 10 carbon atoms, which is particularly preferably selected from succinic acid, malic acid, oxalic acid, malonic acid, adipic acid, pimelic acid, cork acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid, oxaloacetic acid, and/or at least one salt of these acids, as well as mixtures of these compounds, the at least one dicarboxylic acid with 2 to 10 carbon atoms being selected extremely preferably from succinic acid, malic acid and maleic acid, as well as their salts.

Salts of dicarboxylic acids with 2 to 10 carbon atoms preferred by the present disclosure are selected from the mono- and disalts of the anions of succinic acid, malic acid, oxalic acid, malonic acid, adipic acid, pimelic acid, cork acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid and oxaloacetic acid with alkali metal ions, alkaline earth metal ions and the ions of basic amino acids such as arginine, lysine and histidine, in particular with lithium, sodium, potassium, magnesium and calcium ions, and mixtures of these salts.

Succinic acid, which as contemplated herein is particularly preferred, has a melting point in the range of from about 185-187° C. at 1013 mbar and is therefore a solid at about 20° C. Succinic acid salts suitable as contemplated herein are selected from the succinates and hydrogen succinates of alkali metal ions, alkaline earth metal ions and the ions of basic amino acids, such as arginine, lysine and histidine, in particular the lithium, sodium, potassium, magnesium and calcium ions, or the succinates and hydrogen succinates of basic amino acids, such as arginine, lysine and/or histidine, e.g. arginine succinate, and mixtures of these salts. The salts of succinic acid may also contain bound water of crystallization, sodium succinate hexahydrate, which as contemplated herein is particularly preferred.

As contemplated herein, malic acid, which is particularly preferred, is optically active. The racemic DL-malic acid has a melting point at 1013 mbar in the range of from about 131-132° C., so at about 20° C. it is a solid. The enantiomers D-malic acid and L-malic acid each have a melting point in the range of from about 100-101° C. at 1013 mbar. For cost reasons, racemic DL-malic acid is preferred.

Salts of malic acid suitable as contemplated herein are selected from the malates and hydrogen malates of alkali metal ions, alkaline earth metal ions and the ions of basic amino acids, such as arginine, lysine and histidine, especially lithium, sodium, potassium, magnesium and calcium ions, as well as mixtures of these salts, especially disodium malate and dipotassium malate, but also the calcium malate. The abovementioned salts of malic acid, suitable as contemplated herein, may contain bound water of crystallization, in particular disodium malate hemihydrate and disodium malate trihydrate.

Oxalic acid, which is preferred as contemplated herein, has a melting point of about 189.5° C. (anhydrous) at 1013 mbar or, as a dihydrate, a melting point of about 101.5° C. Oxalic acid salts suitable as contemplated herein are selected from the oxalates and hydrogen oxalates of alkali metal ions, alkaline earth metal ions and the ions of basic amino acids, such as arginine, lysine and histidine, in particular lithium, sodium, potassium, magnesium and calcium ions, as well as mixtures of these salts.

Malonic acid, which is preferred as contemplated herein, has a melting point of about 135° C. at 1013 mbar. Salts of malonic acid which are suitable as contemplated herein are selected from the malates and hydrogen malates of alkali metal ions, alkaline earth metal ions and the ions of basic amino acids, such as arginine, lysine and histidine, in particular of lithium, sodium, potassium, magnesium and calcium ions, as well as mixtures of these salts.

The adipic acid preferred in the present disclosure has a melting point of about 152° C. at 1013 mbar. Salts of adipic acid which are suitable as contemplated herein are selected from the adipates and hydrogen adipates of alkali metal ions, alkaline earth metal ions and the ions of basic amino acids, such as arginine, lysine and histidine, especially lithium, sodium, potassium, magnesium and calcium ions, as well as mixtures of these salts.

Pimelic acid, which is preferred as contemplated herein, has a melting point of about 105° C. at 1013 mbar. Salts of pimelic acid suitable as contemplated herein are selected from the pimelates and hydrogen pimelates of alkali metal ions, alkaline earth metal ions and the ions of basic amino acids, such as arginine, lysine and histidine, in particular lithium, sodium, potassium, magnesium and calcium ions, as well as mixtures of these salts.

As contemplated herein, the preferred cork acid has a melting point of about 144° C. at 1013 mbar. Salts of cork acid suitable as contemplated herein are selected from the suberates and hydrogen suberates of alkali metal ions, alkaline earth metal ions and the ions of basic amino acids, such as arginine, lysine and histidine, especially lithium, sodium, potassium, magnesium and calcium ions, and mixtures of these salts.

Azelaic acid, which is the preferred acid as contemplated herein, has a melting point of about 106° C. at 1013 mbar. Salts of azelaic acid which are suitable as contemplated herein are selected from the azelates and hydrogen azelates of alkali metal ions, alkaline earth metal ions and the ions of basic amino acids, such as arginine, lysine and histidine, especially lithium, sodium, potassium, magnesium and calcium ions, as well as mixtures of these salts.

Sebacic acid, which is preferred as contemplated herein, has a melting point of about 134.5° C. at 1013 mbar. Salts of sebacic acid which are suitable as contemplated herein are selected from the sebacates and hydrogen sebacates of alkali metal ions, alkaline earth metal ions and the ions of basic amino acids, such as arginine, lysine and histidine, especially lithium, sodium, potassium, magnesium and calcium ions, as well as mixtures of these salts.

Maleic acid, which as contemplated herein is particularly preferred, has a melting point of from about 130 to about 131° C. at 1013 mbar (from ethanol or benzene) and of from about 138 to about 139° C. (from water). Salts of maleic acid suitable as contemplated herein are selected from the maleates and hydrogen maleates of alkali metal ions and alkaline earth metal ions, of lithium, sodium, potassium, magnesium and calcium ions, and mixtures of these salts.

Fumaric acid, which as contemplated herein is particularly preferred, has a melting point of about 287° C. at 1013 mbar in the sealed tube: at about 200° C., fumaric acid sublimates. Salts of fumaric acid suitable as contemplated herein are selected from the fumarates and hydrogen fumarates of alkali metal ions and alkaline earth metal ions, of lithium, sodium, potassium, magnesium and calcium ions, and mixtures of these salts.

The D-tartaric acid (anticlockwise), which is particularly preferred as contemplated herein, has a melting point of from about 168-170° C. at 1013 mbar. Salts of D-tartaric acid suitable as contemplated herein are selected from the tartrates and hydrogentartrates of alkali metal ions and alkaline earth metal ions, especially lithium, sodium, potassium, magnesium and calcium ions, as well as mixtures of these salts.

The L-tartaric acid (clockwise rotation), which is particularly preferred as contemplated herein, has a melting point of from about 168-170° C. at 1013 mbar. Salts of L-artaric acid suitable as contemplated herein are selected from the tartrates and hydrogentartrates of alkali metal ions and alkaline earth metal ions, especially lithium, sodium, potassium, magnesium and calcium ions, as well as mixtures of these salts.

The meso-tartaric acid, which as contemplated herein is particularly preferred, has a melting point of about 140° C. at 1013 mbar. Salts of meso-tartaric acid suitable as contemplated herein are selected from the tartrates and hydrogentartrates of alkali metal ions and alkaline earth metal ions, in particular lithium, sodium, potassium, magnesium and calcium ions, as well as mixtures of these salts.

As contemplated herein, the racemic mixture of D-tartaric acid and L-tartaric acid is the most preferred grape acid. Grape acid has a melting point of about 206° C. at 1013 mbar. Salts of grape acid suitable as contemplated herein are selected from the tartrates and hydrogentartrates of alkali metal ions and alkaline earth metal ions, of lithium, sodium, potassium, magnesium, and calcium ions, as well as mixtures of these salts.

The alpha-ketoglutaric acid, which as contemplated herein is particularly preferred, has a melting point of from about 112-116° C. at 1013 mbar. Salts of alpha-ketoglutaric acid suitable as contemplated herein are selected from the alpha-ketoglutarates and alpha-ketohydrogen glutarates of alkali metal ions and alkaline earth metal ions, in particular of lithium, sodium, potassium, magnesium and calcium ions, as well as mixtures of these salts.

Beta-ketoglutaric acid, which as contemplated herein is particularly preferred, has a melting point of about 122° C. at 1013 mbar; it melts with decomposition. Salts of beta-ketoglutaric acid suitable as contemplated herein are selected from the beta-ketoglutarates and beta-ketohydrogen glutarates of alkali metal ions and alkaline earth metal ions, in particular of lithium, sodium, potassium, magnesium and calcium ions, and mixtures of these salts.

Oxaloacetic acid, which is particularly favored by the present disclosure, has a melting point of about 161° C. at 1013 mbar. Salts of oxaloacetic acid which are suitable as contemplated herein are selected from the oxaline acetates and oxaline hydrogen acetates of alkali metal ions and alkaline earth metal ions, in particular of lithium, sodium, potassium, magnesium and calcium ions, as well as mixtures of these salts.

Blonding powders preferred as contemplated herein, which contain at least one dicarboxylic acid with 2 to 10 carbon atoms, selected from succinic acid, malic acid, oxalic acid, malonic acid, adipic acid, pimelic acid, cork acid, azelaic acid, sebacic acid, and/or at least one salt of these acids, in a total amount of from about 0.03-7 wt. %, converted to the mass of free dicarboxylic acid. %, preferably from about 0.1-5 wt. %, particularly preferably from about 0.5-3 wt. %, extremely preferably from about 0.9-1.5 wt. %, each based on the weight of the blonding powder.

Further blonding powders preferred as contemplated herein contain succinic acid and/or at least one salt of succinic acid in a total amount, converted to the mass of free dicarboxylic acid, of from about 0.03-7% by weight, preferably from about 0.1-5% by weight, particularly preferably from about 0.5-3% by weight, extremely preferably from about 0.9-1.5% by weight, in each case based on the weight of the blonding powder.

Further blonding powders preferred as contemplated herein contain malic acid and/or at least one salt of malic acid in a total amount, converted to the mass of free dicarboxylic acid, of from about 0.03-7% by weight, preferably from about 0.1-5% by weight, particularly preferably from about 0.5-3% by weight, extremely preferably from about 0.9-1.5% by weight, in each case based on the weight of the blonding powder.

Blonding powders particularly preferred as contemplated herein further contain at least one or more hydrophilic thickeners, preferably selected from polysaccharides, which may be chemically and/or physically modified. As contemplated herein, compounds from the group of polysaccharides are particularly preferred as hydrophilic thickeners, as the basic structures of the polysaccharides are of natural origin and biodegradable. Preferred hydrophilic polysaccharide thickeners are selected from celluloses, cellulose ethers of C1-C4 alcohols, cellulose esters, xanthan gum, alginic acids (and their corresponding physiologically compatible salts, the alginates), Agar Agar (with the polysaccharide agarose as the main component present in agar agar), starch fractions and starch derivatives such as amylose, amylopectin and dextrins, karaya gum, locust bean gum, gum arabic, pectins, dextran and guar gum and mixtures thereof.

Cellulose ethers of C1-C4 alcohols and cellulose esters preferred as contemplated herein are selected from methyl celluloses, ethyl celluloses, hydroxyalkyl celluloses (such as hydroxyethyl cellulose), methylhydroxyalkyl celluloses and carboxymethyl celluloses (such as those with the INCI designation Cellulose Gum) and their physiologically compatible salts.

Carboxymethyl cellulose (preferably carboxymethyl cellulose with the INCI designation Cellulose Gum) is contained in preferred forms as a hydrophilic thickener for reliable viscosity adjustment and residue-free application on keratin fibers and the scalp. Carboxymethyl cellulose may be present in a preferred form as the sole hydrophilic thickener. A combination of carboxymethylcellulose and hydroxyethylcellulose is particularly preferred.

A combination of carboxymethyl cellulose and xanthan (preferably xanthan with the INCI designation xanthan gum) may also be preferred as contemplated herein.

Blonding powders particularly preferred as contemplated herein contain at least one hydrophilic thickener in a total amount of from about 0.1 to about 5% by weight, preferably from about 0.5 to about 4% by weight, more preferably from about 1 to about 3.5% by weight and very particularly preferably from about 2.5 to about 3.4% by weight, in each case based on the weight of the blonding powder.

In a further preferred embodiment of the present disclosure, the blonding powder as contemplated herein contains, in each case based on its weight, from about 0.1 to about 4% by weight, preferably from about 1 to about 2.8% by weight, of carboxymethyl cellulose.

In a further preferred embodiment of the present disclosure, the blonding powder as contemplated herein contains, in each case based on its weight, from about 0.1 to about 3% by weight, preferably from about 0.5 to about 2.5% by weight, more preferably from about 0.7 to about 1.5% by weight, of hydroxyethyl cellulose.

In a further preferred embodiment of the present disclosure, the blonding powder as contemplated herein contains, in each case based on its weight, from about 0.1 to about 3% by weight, preferably from about 0.5 to about 2.5% by weight, more preferably from about 0.7 to about 1.5% by weight, of xanthan gum.

A further object of the present disclosure is a process for brightening keratinous fibers, in particular human hair, in which a blonding powder as contemplated herein is mixed with an oxidation composition (Ox) which, in each case based on its weight, contains from about 50-96% by weight, preferably from about 70-93% by weight, particularly preferably from about 80-90% by weight, water and from about 0.5-20% by weight of a water-based oxidation agent, which may be hydrogen peroxide, and further contains at least one pH adjusting agent in such an amount that the oxidation composition has a pH value in the range of from about 1.5 to about 5.5, measured at about 20° C. This is applied to the keratin-containing fibers immediately thereafter, left on the fibers for from about 5 to about 60 minutes and then the fibers are rinsed with water and optionally washed out with a surfactant-containing cleaning agent, the blonding powder (B) and the oxidation composition (Ox) preferably being present in a ratio (B):(Ox) of 0.2-1, particularly preferred from about 0.3-0.8, further preferred from about 0.4-0.7, extremely preferred from about 0.5-0.6.

A further object of the present disclosure is a process for brightening keratinous fibers, in particular human hair, in which a blonding powder as contemplated herein is mixed with an oxidation composition (Ox) which, in each case based on its weight, contains from about 50-96% by weight, preferably from about 70-93% by weight, particularly preferably from about 80-90% by weight, water and from about 0.5-20% by weight of a water-based oxidation agent, which may be hydrogen peroxide, and further containing at least one pH adjusting agent in such an amount that the oxidation composition (Ox) has a pH in the range of from about 1.5 to about 5.5, measured at about 20° C., and additionally with an alkalizing composition (Alk) which is free of ammonia and ammonium salts and which contains water and at least one alkalizing agent, which is selected from alkanolamines, basic amino acids, alkali hydroxides, and mixtures thereof, and has a pH value in the range from about 8-12, preferably from about 9-11, particularly preferably from about 9.5-10.5, in each case measured at about 20° C., to form an application mixture. The application mixture is applied immediately afterwards to the keratin-containing fibers, left on the fibers for from about 5 to about 60 minutes and then the fibers are rinsed with water and optionally washed out with a surfactant-containing detergent. The blonding powder (B), the oxidizing composition (Ox) and the alkalizing composition (Alk) are preferably in a ratio by weight (B):(Ox):(Alk) from (0.7-1.3):(2-3):(2-3), particularly preferred (0.8-1.2):(2.3-3):(2.3-3), preferably 1:2.5:2.5 or 1:3:3, as mixed together.

In another preferred embodiment of the present disclosure, a blonding powder as contemplated herein can be combined with an alkalizing composition and with an oxidizing composition to form a brightening agent for keratinous fibers.

The alkalizing composition (Alk) used as contemplated herein is free of ammonia and ammonium salts and contains water and at least one alkalizing agent selected from alkanolamines, basic amino acids, alkali hydroxides, and mixtures thereof and also has a pH value in the range of from about 8-12, preferably from about 9-11, particularly preferably from about 9.5-10.5, in each case measured at about 20° C.

Preferred alkanolamines are selected from monoethanolamine, 2-amino-2-methylpropanol, triethanolamine, and mixtures thereof, with monoethanolamine being particularly preferred.

Preferred basic amino acids are selected from arginine, lysine, ornithine, and histidine, as well as the salts of these amino acids, especially the hydrogen halides, especially preferred the hydrogen chlorides. Mixtures of the basic amino acids and/or their salts are also preferred as contemplated herein. Basic amino acids preferred by the present disclosure are selected from arginine, lysine and lysine hydrochloride and mixtures thereof. As contemplated herein, particularly preferred mixtures are selected from arginine/lysine hydrochloride and arginine/lysine.

Preferred alkali hydroxides are selected from sodium hydroxide and potassium hydroxide and mixtures thereof.

In addition to alkanolamines and/or basic amino acids and/or alkali hydroxides, the alkalizing composition (Alk) used as contemplated herein may contain at least one further alkalizing agent selected from alkali metal silicates, alkaline earth metal silicates, alkaline earth metal hydroxide carbonates, alkali metal carbonates, alkali metal hydrogen carbonates, alkaline earth metal hydroxides, alkali metal metasilicates, alkaline earth metal metasilicates and alkaline earth metal hydroxides, as well as mixtures of these substances.

Preferably monoethanolamine is contained in the alkalizing compositions preferably used as contemplated herein in amounts of from about 0.01-10 wt. %, preferably from about 0.1-7.5 wt. %, more preferably from about 0.5-5.5 wt. % and particularly preferably from about 1.5-4.5 wt. %—each based on the weight of the alkalizing composition.

The oxidation composition (Ox) used in the whitening process as contemplated herein essentially contains water and hydrogen peroxide. The concentration of hydrogen peroxide is determined on the one hand by the legal requirements and on the other hand by the desired effect. It is from about 0.5-20% by weight, preferably from about 3-12% by weight, particularly preferably from about 6-9% by weight of hydrogen peroxide (calculated as 100% $H_2O_2$), each based on the weight of the oxidation composition (Ox).

To stabilize the hydrogen peroxide, the oxidation composition (Ox) preferably has an acidic pH value, in particular a pH value in the range of from about 1.5 to about 5.5, measured at about 20° C. To stabilize the hydrogen peroxide, it also contains preferably complexing agents, preservatives, stabilizing agents and/or buffer substances.

As contemplated herein, the blonding powder is preferably composed in such a way that the mixture with the aforementioned oxidation composition (Ox), i.e. the ready-to-use brightening agent, has an alkaline pH value, preferably a pH value of from about 8.5 to about 12, particularly preferably a pH value of from about 9.0 to about 11.5, extremely preferably a pH value of from about 9.5 to about 11.0, in each case measured at about 20° C.

Oxidation compositions (Ox) used with particular preference as contemplated herein further contain at least one oil and/or at least one fat component with a melting point in the range of from about 23-110° C., preferably in a total amount of from about 0.1-60% by weight, particularly preferably from about 0.5-40% by weight, extremely preferably from about 2-24% by weight, in each case based on the weight of the oxidation composition (Ox) preferably used as contemplated herein. The oils suitable for the oxidation compositions (Ox) preferred by the present disclosure are, for the most part, the same oils that are revealed above as suitable dust removal agents.

Oxidizing compositions (Ox) particularly preferred as contemplated herein contain at least one oil selected from the benzoic acid esters of linear or branched C8-22 alkanols. Benzoic acid C12-C15 alkyl esters are particularly preferred.

Other oils suitable for oxidation compositions (Ox), which as contemplated herein are particularly preferred, are selected from the triglycerides (=triple esters of glycerol) of linear or branched, saturated, optionally hydroxylated C8-30 fatty acids. Preferred are saturated triglyceride oils, especially Capric/Caprylic Triglycerides.

Other oils suitable for oxidation compositions (Ox) which are particularly preferred as contemplated herein are selected from the dicarboxylic acid esters of linear or branched $C_2$-$C_{10}$ alkanols, especially diisopropyl adipate, Di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Other oils suitable for oxidation compositions (Ox) preferably used as contemplated herein are selected from the esters of linear or branched saturated fatty alcohols having 2-30 carbon atoms with linear or branched saturated fatty acids having 2-30 carbon atoms, which may be hydroxylated. These include preferably 2-hexyl decyl stearate, 2-hexyl decyl laurate, isodecyl neopentanoate, isononyl isononanoate, 2-ethylhexyl palmitate and 2-ethylhexyl stearate, isopropyl myristate, isopropyl palmitate, isopropyl stearate, isopropyl isostearate, isooctyl stearate, isonononyl stearate, Isocetylstearate, isononnonylisononanoate, isotridecylisononanoate, cetearylisononanoate, 2-ethylhexyl laurate, 2-ethylhexyl isostearate, 2-ethylhexyl cocoate, 2-octyl-dodecyl palmitate, butyloctanoic acid 2-butyloctanoate, diisotridecyl acetate, n-butyl stearate and n-hexyl laurate.

Other oils suitable for oxidation compositions (Ox), which as contemplated herein are particularly preferred, are selected from the $C_8$-$C_{22}$ fatty alcohol esters of monovalent or polyvalent $C_2$-$C_7$ hydroxycarboxylic acids, especially the esters of glycolic acid, lactic acid, malic acid, tartaric acid, citric acid and salicylic acid, e.g. $C_{12}$-$C_{15}$ alkyl lactate.

Other oils suitable for oxidation compositions (Ox) particularly preferred as contemplated herein are selected from the symmetrical, asymmetrical or cyclic esters of carbonic acid with $C_{3-22}$ alkanols, $C_{3-22}$ alkanediols or $C_{3-22}$ alkanetriols, e.g. dicaprylylcarbonate, or the esters according to DE19756454 A1, especially glycerin carbonate.

Preferred oxidizing compositions (Ox) used as contemplated herein contain at least one oil selected from the benzoic acid esters of linear or branched $C_{8-22}$ alkanols; triglycerides of linear or branched, saturated, optionally hydroxylated $C_{8-30}$ fatty acids; the dicarboxylic acid esters of linear or branched $C_2$-$C_{10}$ alkanols; the esters of linear or branched saturated fatty alcohols having 2-30 carbon atoms with linear or branched saturated fatty acids having 2-30 carbon atoms, which may be hydroxylated; the $C_8$-$C_{22}$ fatty alcohol esters of monovalent or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$ fatty acids (dimer fatty acids) with monovalent linear, branched or cyclic $C_2$-$C_{18}$ alkanols or with polyvalent linear or branched $C_2$-$C_6$ alkanols, and mixtures of the above substances.

Fat components with a melting point in the range of 23-110° C. preferably used in the oxidation compositions (Ox) as contemplated herein are selected from linear saturated 1-alkanols with 12-30 carbon atoms, preferably in a total amount of from about 0.1-8 wt. %, particularly preferably from about 3.0 to about 6.0 wt. %, each based on the weight of the oxidation composition (Ox) used as contemplated herein.

Preferably the at least one linear saturated 1-alkanol with 12-30 carbon atoms are selected from lauryl alcohol, myristyl alcohol, cetyl alcohol, stearyl alcohol, arachidyl alcohol, and behenyl alcohol as well as mixtures of these 1-alkanols, especially preferably cetyl alcohol, stearyl alcohol and cetyl alcohol/stearyl alcohol mixtures.

Oxidation compositions (Ox) preferably used as contemplated herein further contain, in each case based on their weight, at least one linear saturated 1-alkanol having 12-30 carbon atoms in a total amount of from about 0.1-8% by weight, preferably in a total amount of from about 2-6% by weight, at least one 1-alkanol selected from cetyl alcohol, stearyl alcohol and cetyl alcohol/stearyl alcohol mixtures being present.

Other oxidation compositions (Ox), which are preferably used as contemplated herein, contain at least one fat component with a melting point in the range of from about 23-110° C., which is selected from esters of a saturated, monovalent $C_{16}$-$C_{60}$ alkanol and a saturated $C_8$-$C_{36}$ monocarboxylic acid, in particular cetyl behenate, stearyl behenate and $C_{20}$-$C_{40}$ alkyl stearate, glycerol triesters of saturated linear $C_{12}$-$C_{30}$ carboxylic acids, which may be hydroxylated, candelilla wax, carnauba wax, beeswax, saturated linear $C_{14}$-$C_{36}$ carboxylic acids and mixtures of the above substances.

Other oxidation compositions (Ox) preferably used as contemplated herein contain at least one surfactant or at least one emulsifier, preferably in a total amount of from about 0.5-10% by weight, preferably from about 1-5% by weight, each based on the weight of the oxidation composition (Ox) used as contemplated herein.

For the purposes of the present application, surfactants and emulsifiers are amphiphilic (bifunctional) compounds which include at least one hydrophobic and at least one hydrophilic part of the molecule. The hydrophobic residue is preferably a hydrocarbon chain with 8-28 carbon atoms, which can be saturated or unsaturated, linear, or branched. This $C_8$-$C_{28}$-Alkyl chain is particularly preferably linear. Basic properties of surfactants and emulsifiers are the oriented absorption at interfaces as well as the aggregation to micelles and the formation of lyotropic phases.

As contemplated herein, anionic, non-ionic, and cationic surfactants are particularly suitable. However, zwitterionic and amphoteric surfactants are also very suitable.

All anionic surfactants suitable for use on the human body are suitable as anionic surfactants in the compositions as contemplated herein. These are exemplified by a water-solubilizing anionic group such as a carboxylate, sulfate, sulfonate or phosphate group and a lipophilic alkyl group with 8 to 30 C atoms. In addition, glycol or polyglycol ether groups, ester, ether, amide and hydroxyl groups may also be present in the molecule. Examples of suitable anionic surfactants are linear and branched fatty acids with 8 to 30 C atoms (soaps), alkyl ether carboxylic acids, acyl sarcosides, acyl taurides, acyl isethionates, sulfosuccinic acid mono-, dialkyl esters and sulfosuccinic acid mono-alkyl polyoxyethyl esters, linear alkane sulfonates, linear alpha-olefin sulfonates, alkyl sulfates. alkyl ether sulfates, and alkyl and/or alkenyl phosphates. Preferred anionic surfactants are alkyl sulfates, alkyl ether sulfates and alkyl ether carboxylic acids each with 10 to 18 C atoms, preferably 12 to 14 C atoms in the alkyl group and up to 12 glycol ether groups, preferably 2 to 6 glycol ether groups in the molecule. Examples of such surfactants are the compounds with the INCI designations sodium laureth sulfates, sodium lauryl sulfates, sodium myreth sulfates or sodium laureth carboxylates.

Zwitterionic surfactants are surface-active compounds which carry at least one quaternary ammonium group and at least one carboxylate, sulfonate or sulfate group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Amphoteric surfactants are surface-active compounds which, apart from a $C_8$-$C_{24}$ alkyl or acyl group, contain at least one free amino group and at least one —COOH or —$SO_3H$ group in the molecule and can form internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycine, N-alkyltaurines, N-alkylsarcosines, 2-alkylaminopropionic acids and alkylaminoacetic acids each with 8 to 24 C atoms in the alkyl group. Particularly preferred amphoteric surfactants are N-cocoalkylaminopropionate, cocoacylaminoethylaminopropionate and $C_{12}$-$C_{18}$-Acylsarcosine.

Nonionic surfactants contain e.g. a polyol group, a polyalkylene glycol ether group or a combination of polyol and polyglycol ether group as the hydrophilic group. Such compounds are, for example, addition products of 4 to 50 mol ethylene oxide and/or 0 to 5 mol propylene oxide to linear and branched fatty alcohols, to fatty acids and to alkylphenols, each with 8 to 20 C atoms in the alkyl group, ethoxylated mono-, di- and triglycerides, such as glycerol monolaurate+20 ethylene oxide, and glycerol monostearate+20 ethylene oxide, sorbitan fatty acid esters and adducts of ethylene oxide with sorbitan fatty acid esters such as polysorbates (Tween 20, Tween 21, Tween 60, Tween 61, Tween 81), adducts of ethylene oxide with fatty acid alkanolamides and fatty amines, and alkyl polyglycosides. $C_8$-$C_{22}$ alkyl mono- and oligoglycosides and their ethoxylated analogues and ethylene oxide addition products to saturated or unsaturated linear fatty alcohols with 2 to 30 moles of ethylene oxide per mole of fatty alcohol are particularly suitable as nonionic surfactants.

Further oxidation compositions preferably used as contemplated herein include at least one anionic surfactant that is selected from alkyl sulfates, alkyl ether sulfates and alkyl ether carboxylic acids each having 10 to 18 C-atoms, preferably 12 to 14 C atoms in the alkyl group and up to 12, preferably 2 to 6, glycol ether groups in the molecule.

Other oxidation compositions preferably used as contemplated herein include at least one nonionic surfactant selected from ethylene oxide adducts to saturated or unsaturated linear fatty alcohols with 2 to 30 moles of ethylene oxide per mole of fatty alcohol, and at least one anionic surfactant selected from alkyl sulfates, alkyl ether sulfates and alkyl ether carboxylic acids each having 10 to 18 C atoms, preferably 12 to 14 C atoms in the alkyl group and up to 12, preferably 2 to 6 glycol ether groups, in the molecule, the weight ratio of the total of all anionic surfactants to the total of all nonionic surfactants being particularly preferably in the range of 5-50, preferably 10-30.

In principle, all cationic surface-active substances suitable for use on the human body are suitable as cationic surfactants in oxidation compositions (Ox) which are preferably used as contemplated herein. These are exemplified by at least one water-solubilizing, cationic group, such as a quaternary ammonium group, or by at least one water-solubilizing, cationisable group, such as an amine group, and furthermore at least one (lipophilically acting) alkyl group with 6 to 30 C atoms or at least one (lipophilically acting) imidazole group or at least one (lipophilically acting) imidazylalkyl group.

Oxidation compositions (Ox) which are used with particular preference as contemplated herein contain at least one cationic surfactant which is preferably selected from quaternary ammonium compounds having at least one C8-C24 alkyl radical, esterquats and amidoamines each having at least one C8-C24 acyl radical, and mixtures thereof. Preferred quaternary ammonium compounds with at least one C8-C24 alkyl radical are ammonium halides, especially chlorides, and ammonium alkyl sulfates, such as methosulfates or ethosulfates, such as C8-C24 alkyl trimethylammonium chlorides, C8-C24 dialkyldimethylammonium chlorides and C8-C24 trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, as well as the imidazolium compounds known under the INCI designations Quaternium-27, Quaternium-83, Quaternium-87 and Quaternium-91. The alkyl chains of the surfactants mentioned above preferably have 8 to 24 carbon atoms.

Esterquats are cationic surfactants which contain both at least one ester function and at least one quaternary ammonium group as a structural element and at least one C8-C24 alkyl or C8-C24 acyl radical. Preferred esterquats are quaternized ester salts of fatty acids with triethanolamine, quaternized ester salts of fatty acids with diethanolalkylamines and quaternized ester salts of fatty acids with 1,2-dihydroxypropyl dialkylamines N,N-bis(2-palmitoyloxyethyl)dimethylammonium chloride, distearoylethyl dimonium methosulfates and distearoylethyl hydroxyethylmonium methosulfates are preferred examples of such esterquats.

Alkylamidoamines are usually produced by amidation of natural or synthetic C8-C24 fatty acids and fatty acid sections with di-(C1-C3)alkylaminoamines A compound from this substance group which is particularly suitable as contemplated herein is stearamidopropyldimethylamine.

Oxidation compositions (Ox) used with particular preference as contemplated herein contain at least one cationic surfactant in a total amount of from about 0.01-5% by weight, preferably from about 0.1-3% by weight, particularly preferably from about 0.3-2% by weight, each based on the weight of the oxidation composition (Ox) used as contemplated herein.

A further object of the present disclosure is a multi-component unit (kit-of-parts) for the brightening of keratinous fibers, which contains at least two separately packaged components, and wherein
i) the first component (I) is a blonding powder as contemplated herein or a preferred blonding powder as contemplated herein,
ii) the second component (II) is an oxidation composition containing, in each case based on its weight, from about 50-96%, preferably from about 70-93%, particularly preferably from about 80-90%, by weight of water and from about 0.5-20% by weight of hydrogen peroxide and having a pH in the range of from about 1.5 to about 5.5, measured at about 20° C.,
where components (I) and (II) are preferably in a weight-related ratio (I):(II) of from about 0.2-1, particularly preferred from about 0.3-0.8, further preferred from about 0.4-0.7, extremely preferred from about 0.5-0.6.

As contemplated herein, the blonding powder of the 3-component kit is preferably composed in such a way that the mixture with the aforementioned oxidation composition (Ox) and with the aforementioned alkalizing composition (Alk), i.e. the ready-to-use brightening agent, has an alkaline pH value, preferably a pH value of from about 8.5 to about 12.0, particularly preferably a pH value of from about 9.0 to about 11.5, extremely preferably a pH value of from about 9.5 to about 11.0, in each case measured at about 20° C.

The ready-to-use mixtures of a blonding powder as contemplated herein or preferred as contemplated herein with one of the aforementioned oxidation compositions (Ox) and optionally with one of the aforementioned alkalizing compositions (Alk) preferably have a viscosity in the range of from about 15,000 to about 100,000 mPas, particularly preferably from about 20,000 to about 85,000 mPas, in each case measured at about 20° C. with a Brookfield viscometer type DV-II+, spindle 5 at a speed of about 4 rpm. A viscosity in this range allows the ready-to-use agent to be easily applied on the one hand and on the other hand to have such a flow behavior that it guarantees a sufficiently long exposure time for the agent to act on the keratinic fibers at the place of action.

In order to facilitate the miscibility of the alkalizing composition used as contemplated herein with the blonding powder and the oxidizing composition used as contemplated herein and to improve the application properties of the resulting application mixture, the alkalizing composition preferably used as contemplated herein contains preferably, in each case based on its weight, at least one surfactant in a total amount of from about 0.5-10% by weight, preferably from about 2-8% by weight.

The surfactants suitable for the alkalizing compositions (Alk) preferably used as contemplated herein are selected from the same anionic, cationic, nonionic, amphoteric and zwitterionic surfactants and emulsifiers disclosed above as surfactants and emulsifiers suitable for the preferably used oxidizing compositions (Ox).

Alkalizing compositions (Alk) used with particular preference as contemplated herein further contain at least one oil and/or at least one fat component with a melting point in the range of from about 23-110° C., preferably in a total amount of from about 0.1-60% by weight, particularly preferably from about 0.5-40% by weight, extremely preferably from about 2-24% by weight, in each case based on the weight of the alkalizing composition (Alk) preferably used as contemplated herein. The oils suitable for the alkalizing compositions (Alk) preferred in the present disclosure are the same oils disclosed above as suitable dust removal agents.

Fat components with a melting point in the range of from about 23-110° C. preferably used in the alkalizing compositions (Alk) as contemplated herein are selected from linear saturated 1-alkanols with 12-30 carbon atoms, preferably in a total amount of from about 0.1-20% by weight, particularly preferably from about 3-15% by weight, extremely preferably from about 5-10% by weight, in each case based on the weight of the alkalizing composition used as contemplated herein.

Preferably the at least one linear saturated 1-alkanol with 12-30 carbon atoms is selected from lauryl alcohol, myristyl alcohol, cetyl alcohol, stearyl alcohol, arachidyl alcohol, and behenyl alcohol as well as mixtures of these 1-alkanols, especially preferably cetyl alcohol, stearyl alcohol and cetyl alcohol/stearyl alcohol mixtures.

Alkalizing compositions (Alk) preferably used as contemplated herein further contain, in each case based on their weight, at least one linear saturated 1-alkanol having 12-30 carbon atoms in a total amount of from about 0.1-20% by weight, preferably in a total amount of from about 3-15% by weight, extremely preferably from about 5-10% by weight, wherein at least one 1-alkanol is selected from cetyl alcohol, stearyl alcohol and cetyl alcohol/stearyl alcohol mixtures.

Other alkalizing compositions (Alk), which are preferably used as contemplated herein, contain at least one fat component with a melting point in the range of from about 23-110° C., which is selected from esters of a saturated, monovalent $C_{16}$-$C_{60}$ alkanol and a saturated $C_8$-$C_{36}$ monocarboxylic acid, in particular cetyl behenate, stearyl behenate and $C_{20}$-$C_{40}$ alkyl stearate, glycerol triesters of saturated linear $C_{12}$-$C_{30}$ carboxylic acids, which may be hydroxylated, candelilla wax, carnauba wax, beeswax, saturated linear $C_{14}$-$C_{36}$ carboxylic acids and mixtures of the above substances.

A multi-component unit comprises several individual components, which are assembled separately from each other, and a common packaging for these components, for example a folding carton. Here the components are provided separately in different containers. In the context of the present disclosure, a container is understood to be an enclosure in the form of a bottle, a tube, a can, a sachet, a sachet, or a similar wrapping, which may be re-closable. According to the present disclosure there are no limits to the wrapping material. Preferably, however, these are wrappings made of glass or plastic.

In addition, the packaging unit may include application aids such as combs, brushes or paint brushes, personal protective clothing, especially disposable gloves, and instructions for use.

The ready-to-use mixtures of a blonding powder according to the present disclosure with one of the aforementioned oxidation compositions (Ox) preferably have a viscosity in the range of from about 15,000 to about 100,000 mPas, particularly preferably from about 20,000 to about 85,000 mPas, each measured at 20° C. with a Brookfield viscometer type DV-II+, spindle 5 at a speed of 4 rpm. A viscosity in this range allows the ready-to-use agent to be easily applied on the one hand and on the other hand to have such a flow behavior that it guarantees a sufficiently long exposure time for the agent to act on the keratinic fibers at the place of action.

Furthermore, the blonding powders and/or the alkalizing compositions preferred as contemplated herein may contain at least one direct dye. These are dyes that are applied directly to the hair and do not require an oxidative process to form the color. For matting undesirable residual color impressions caused by melanin decomposition products, especially in the reddish or bluish area, certain direct dyes of complementary colors are particularly preferred. Direct dyes are usually nitrophenylenediamines, nitroaminophenols, azo dyes, anthraquinones or indophenols. Direct dyes can be anionic, cationic, or non-ionic. The direct dyes are each preferably contained in an amount of from about 0.001 to about 2% by weight, based on the weight of the bleaching powder or alkalizing composition (Alk).

Preferred anionic direct dyes are the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromphenol Blue and Tetrabromophenol Blue. Preferred cationic direct dyes are cationic triphenylmethane dyes, for example Basic Blue 7, Basic Blue 26, Basic Violet 2 and Basic Violet 14, aromatic systems substituted with a quaternary nitrogen group, such as Basic Yellow 57, Basic Red 76, Basic Blue 99, Basic Brown 16 and Basic Brown 17, cationic anthraquinone dyes such as HC Blue 16 (Bluequat B) and direct dyes containing a heterocycle containing at least one quaternary nitrogen atom, in particular Basic Yellow 87, Basic Orange 31 and Basic Red 51. The cationic direct dyes marketed under the trademark Arianor® are, as contemplated herein, also preferred cationic direct dyes. Non-ionic direct dyes are particularly suitable, such as nitro and quinone dyes and neutral azo dyes. Preferred non-ionic direct dyes are those under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-di-amino-2-nitrobenzene, 2-amino-4-nitrophenol, 1,4-bis-(2-hydroxyethyl)-amino-2-nitrobenzene, 3-nitro-4-(2-hydroxyethyl)aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol. A combination of tetrabromophenol blue and Acid Red 92 is particularly preferred.

Preferably the exposure time is from about 5 to about 60 min, especially from about 5 to about 50 min, especially preferably from about 10 to about 45 min. During the exposure time of the agents on the fiber it can be advantageous to support the whitening process by adding heat. An exposure phase at room temperature is also according to the present disclosure. In particular, the temperature during the exposure time is between about 20° C. and about 40° C., especially between about 25° C. and about 38° C. The agents give good treatment results even at physiologically compatible temperatures below about 45° C.

At the end of the whitening process, all components found on the keratin fibers are rinsed from the hair with water or a surfactant-based detergent. In particular, commercially available shampoo can be used as a cleaning agent, whereby the cleaning agent can be dispensed with and the rinsing process, or the rinsing process can be carried out with tap water if the whitening agent has a higher surfactant content.

What has been said about the blonding powders according to the present disclosure and preferred according to the present disclosure applies mutatis mutandis to the multi-component units (kits of parts) according to the present disclosure and preferred according to the present disclosure.

What has been said about the blonding powders as contemplated herein and preferred in the present disclosure applies mutatis mutandis also to the processes for brightening keratinous fibers as contemplated herein and preferred in the present disclosure.

What has been said about the oxidizing compositions or alkalizing compositions used as contemplated herein and preferred as contemplated herein also applies mutatis mutandis to the multi-component units (kits of parts) used as contemplated herein and preferred as contemplated herein.

The foregoing with respect to oxidizing or alkalizing compositions used as contemplated herein and preferred in the present disclosure also applies mutatis mutandis to the process for brightening keratinous fibers, as defined in the present disclosure, and preferred as contemplated herein.

What has been said about the blonding powders as contemplated herein and preferred as contemplated herein applies mutatis mutandis also to the use as contemplated herein.

What has been said about the oxidizing compositions or alkalizing compositions used preferentially as contemplated herein and as contemplated herein also applies mutatis mutandis to the use as contemplated herein.

EXAMPLES

1. Blonding powder components of the Blonding Kit as contemplated herein (unless otherwise stated, the quantities correspond to weight-%)

|  | No. 1.1 | No. 1.2 | No. 1.3 | No. 1.4 |
|---|---|---|---|---|
| Sodium metasilicate | 4.1 | 4.5 | 4.7 | 6.0 |
| Sodium silicate | 17.6 | 17.6 | 17.6 | 17.6 |
| Magnesium carbonate hydroxide | 34.5 | 41.8 | 27.85 | 13.75 |
| Cellulose Gum | 2.8 | 2.5 | 2.5 | 2.5 |
| Hydroxyethyl cellulose | 0.7 | 0.35 | 0.65 | 0.85 |
| Tetrasodium EDTA | 0.4 | 0.4 | 0.5 | 0.6 |
| Potassium persulfate | 14.4 | 15 | 18 | 21 |
| Silica | 3.0 | 3 | 3 | 3 |
| Potassium sulfate | 0.2 | 0.2 | 0.3 | 0.4 |
| Sodium sulfate | 0.1 | 0.05 | 0.1 | 0.2 |
| Sodium persulfate | 8.5 | 4 | 10 | 15 |
| Polyquaternium-4 | 0.1 | 0.2 | 0.3 | 0.4 |
| Octyldodecanol | 11.6 | 8 | 11 | 14.1 |
| Dicaprylyl Ether | 2.0 | 2.4 | 3.5 | 4.6 |
|  | 100.0 | 100.0 | 100.0 | 100.0 |

2. Developer emulsion=oxidizing composition (Ox) of the blonding kit as contemplated herein

| Ingredient | Quantity (% by weight) |
|---|---|
| Dipicolinic acid (2,6-dicarboxypyridine) | 0.1 |
| Potassium hydroxide | 0.13 |
| Etidronic acid | 0.24 |
| Sodium cetaryl sulfate | 0.3 |
| Cetearyl alcohol | 3.6 |
| Ceteareth-20 | 0.5 |
| PEG-40 Castor Oil | 0.6 |
| Isopropyl myristate | 10.0 |
| Disodium pyrophosphate | 0.1 |
| Beeswax | 0.3 |
| Hydrogen peroxide | 5.54 |
| Water | ad 100 |

3. Preparation of a bleaching cream=alkalizing agent component of the bleaching kit as contemplated herein An alkalizing composition (Alk), also known as bleaching cream, was produced from the components listed below:

| Hydrenol D | 8.00 |
|---|---|
| Eumulgin B2 | 0.45 |
| Lorol. C12-C18 techn. | 3.00 |
| Texapon NSO | 16.00 |
| Dehyton K | 10.00 |
| Monoethanolamine | 8.00 |
| L-arginine | 1.00 |
| Etidronic acid | 0.12 |
| Sodium silicate 40/42v | 0.50 |
| Water | ad 100 |

Hydrenol D—C16-$C_{18}$-Fatty alcohol (INCI designation: Cetearyl alcohol) (BASF)
Eumulgin B2—INCI designation: Ceteareth-20 (BASF)
Lorol. C12-C18 techn.:—$C_{12}$-$C_{18}$-Fatty alcohol (INCI designation: Coconut alcohol) (BASF)
Texapon NSO—Sodium lauryl ether sulfate (27% by weight active substance in water; INCI: Sodium Laureth Sulfate) (BASF)
Dehyton K—approx. 30 wt. % active substance; INCI designation: Cocamidopropyl Betaine (BASF)

Initially, Hydrenol D, Eumulgin B2 and Lorol. C12-C18 techn., Texapon NSO and Dehyton K melted together at 80° C. This melt was mixed with part of the water quantity and the mixture was stirred vigorously. With further stirring, the indicated quantities of the remaining ingredients were then added, and the recipe could cool to room temperature.

4. Production and use of a bleaching agent as contemplated herein including three components One each of the above mentioned bleaching powders (B) 1.1 or 1.2 was mixed with the developer emulsion (Ox) according to section 2 and the bleaching cream (Alk) from section 3 in the weight ratio (B):(Ox):(Alk) of 1:2.5:2.5.

The pH value of this ready-to-use application mixture was between 9.5 and 11, measured at 20° C. For the bleaching process, 4 times the amount of the finished application mixture was applied to dry dark blonde hair strands (Kerling 6/0) of approx. 0.7 g weight (4 g application mixture per gram of hair). After the strands were bleached for 45 min at 35° C., they were washed with water for 2 minutes and dried with a hairdryer.

5. Whitening performance

By colorimetric measurement with a colorimeter, the delta L value ($B_{leached\ strands}$-$L_{bleached}$ area) as a measure of the whitening performance.

|  | Bleaching powder 1.1 with developer and bleaching cream | Bleaching powder 1.2 with developer and bleaching cream |
|---|---|---|
| ΔL | 28.3 | 30.2 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A multi-component unit (kit-of-parts) for brightening keratinous fibers, comprising at least three separately packaged components, wherein
   i) the first component is a blonding powder (B) comprising;
      a) at least one oxidizing agent selected from the group of sodium salts of a peroxosulfuric acid, potassium salts of the peroxosulfuric acid, and mixtures thereof,
      b) from about 0.1 to about 15% by weight of at least one branched fatty alcohol with 8-24 carbon atoms, based on a weight of the blonding powder,
      c) from about 0.1 to about 15% by weight of at least one dialkyl ether with 6 to 18 C atoms in the alkyl group, based on the weight of the blonding powder, and
      d) from about 0 to about 8% by weight of water, based on the weight of the blonding powder,
      e) wherein the blonding powder comprises from about 0.2 to about 20% by weight of oils, including components b) and c), based on the weight of the blonding powder, and
      f) wherein the blonding powder does not comprise ammonium compounds, paraffin oil, mineral oil, or silicone compounds,
   ii) the second component is an oxidizing composition (Ox)comprising, in each case based on its weight from about 50 to about 96%, by weight of water and from about 0.5 to about 20% by weight of hydrogen peroxide, wherein the oxidizing composition (Ox) has a pH in the range of from about 1.5 to about 5.5, measured at about 20° C., iii) the third component is an alkalizing composition (Alk) which is free from ammonia and ammonium salts and which comprises water and at least one alkalizing agent selected from the group of alkanolamines, basic amino acids, alkali hydroxides, and mixtures thereof, wherein the alkalizing composition (Alk) has a pH in the range of from about 8 to about 12 measured at about 20° C., wherein the blonding powder (B), the oxidizing composition (Ox) and the alkalizing composition (Alk) are present in a weight ratio (B): (Ox): (Alk) from (0.7-1.3): (2-3): (2-3).

2. The kit-of-parts according to claim 1, wherein the at least one oxidizing agent is included in the blonding powder (B) in a total amount of from about 5-85% based on the weight of the blonding powder (B).

3. The kit-of-parts according to claim 1, wherein the blonding powder additionally comprises at least one inorganic alkalizing agent which is solid at about 20° C. and 1013 mbar in a total amount of from about 0.1 to about 50% by weight, based on the weight of the blonding powder, wherein the inorganic alkalizing agent comprises at least one sodium silicate or sodium metasilicate with a molar $SiO_2/Na_2O$ ratio of ≥2.

4. The kit-of-parts according to claim 1, wherein the at least one dialkyl ether having 6 to 18 C atoms in the alkyl group is selected from the group of di-n-alkyl ethers having a total of 12 to 36 C atoms, dialkyl ethers with branched alkyl groups each having 6 to 18 C atoms, and combinations thereof.

5. The kit-of-parts according to claim 4, wherein the at least one dialkyl ether having 6 to 18 C atoms in the alkyl group is selected from the group of di-n-octyl ether, di-n-decyl ether, di-n-nonyl ether, di-n-undecyl ether, di-n-dodecyl ether, di-n-octadecyl ether, n-hexyl-n-octyl ether, n-octyl-n-decyl ether, n-decyl-n-undecyl ether, n-undecyl-n-dodecyl ether, n-hexyl-n-undecyl ether, di-(2-ethylhexyl) ether, di-(2-ethyldecyl) ether, and mixtures thereof.

6. The kit-of-parts according to claim 1, wherein the at least one branched fatty alcohol with 8-24 carbon atoms is selected from the group of 2-octyldodecanol, 2-hexyldecanol, 2-ethylhexyl alcohol, isostearyl alcohol, and mixtures thereof.

7. The kit-of-parts according to claim 1, wherein the at least one oxidizing agent a) is selected from the group of sodium peroxodisulfate, potassium peroxodisulfate, sodium percarbonate, sodium peroxomonosulfate, potassium peroxomonosulfate, and mixtures of these compounds.

8. The kit-of-parts according to claim 1, wherein the blonding powder comprises from about 1 to about 17% by weight of the oils, including components b) and c), based on the weight of the blonding powder.

9. The kit-of-parts according to claim 1, wherein the weight ratio of the total amount of branched fatty alcohols with 8-24 carbon atoms to the total amount of dialkyl ethers with 6 to 18 carbon atoms in the alkyl group in blonding powder (B) is from about 2 to about 8.

10. A method for brightening keratinous fibers, the method comprising the steps of:

mixing a blonding powder (B) with an oxidizing composition (Ox) and an alkalizing composition (Alk) to form an application mixture, wherein the blonding powder (B) comprises, a) at least one oxidizing agent selected from the group of sodium salts of a peroxosulfuric acid, potassium salts of the peroxosulfuric acid, and mixtures thereof, b) from about 0.1 to about 15% by weight of at least one branched fatty alcohol with 8-24 carbon atoms, based on a weight of the blonding powder, c) from about 0.1 to about 15% by weight of at least one dialkyl ether with 6 to 18 C atoms in the alkyl group, based on the weight of the blonding powder, d) and from 0 to about 8% by weight of water, based on the weight of the blonding powder, e) wherein the blonding powder comprises from about 0.2 to about 20% by weight of oils, including components b) and c), based on the weight of the blonding powder, and f) wherein the blonding powder does not comprise ammonium compounds, paraffin oil, mineral oil, or silicone compounds, wherein the oxidizing composition (Ox) comprises, in each case based on its weight, from about 50 to about 96% by weight of water, from about 0.5 to about 20% by weight of hydrogen peroxide, and at least one pH adjusting agent in such an amount that the oxidizing composition (Ox) has a pH in the range from about 1.5 to about 5.5, measured at about 20° C., and wherein the alkalizing composition (Alk) is free from ammonia and ammonium salts, and wherein the alkalizing composition (Alk) comprises water and at least one alkalizing agent selected from the group of alkanolamines, basic amino acids, alkali hydroxides, and mixtures thereof, and has a pH in the range of from about 8 to about 12 measured at about 20° C., applying the application mixture to the keratin-containing fibers;

leaving the application mixture on the keratin-containing fibers for from about 5 to about 60 minutes; and rinsing the keratin-containing fibers with water; and optionally washing the keratin-containing fibers with a surfactant-containing detergent, wherein the blonding powder (B), the oxidizing composition (Ox) and the alkalizing composition (Alk) are present in the application mixture in a weight ratio (B):(Ox):(Alk) of (0.7-1.3):(2-3):(2-3).

11. The method for brightening keratinous fibers, of claim 10 wherein:

the at least one oxidizing agent is included in the blonding powder (B) in a total amount of from about 5-85%, based on the weight of the blonding powder (B).

12. The method for brightening keratinous fibers of claim 10, wherein:

the blonding powder (B) additionally comprises at least one inorganic alkalizing agent, wherein the at least one inorganic alkalizing agent is solid at about 20° C. and 1013 mbar, in a total amount of from about 0.1 to about 50% by weight, based on the weight of the blonding powder, wherein the inorganic alkalizing agent comprises at least one sodium silicate or sodium metasilicate with a molar $SiO_2/Na_2O$ ratio of ≥2.

13. The method for brightening keratinous fibers of claim 10, wherein:

the at least one dialkyl ether having 6 to 18 C atoms in the alkyl group is selected from the group of di-n-alkyl ethers having a total of 12 to 36 C atoms, dialkyl ethers with branched alkyl groups each having 6 to 18 C atoms, and combinations thereof.

14. The method for brightening keratinous fibers of claim 10, wherein:

the at least one dialkyl ether having 6 to 18 C atoms in the alkyl group is selected from the group of di-n-octyl ether, di-n-decyl ether, di-n-nonyl ether, di-n-undecyl ether, di-n-dodecyl ether, di-n-octadecyl ether, n-hexyl-n-octyl ether, n-octyl-n-decyl ether, n-decyl-n-undecyl ether, n-undecyl-n-dodecyl ether, n-hexyl-n-undecyl ether, di-(2-ethylhexyl) ether, di-(2-ethyldecyl) ether, and mixtures thereof.

15. The method for brightening keratinous fibers of claim 10, wherein:
the at least one branched fatty alcohol with 8-24 carbon atoms is selected from the group of 2-octyldodecanol, 2-hexyldecanol, 2-ethylhexyl alcohol, isostearyl alcohol, and mixtures thereof.

16. The method for brightening keratinous fibers of claim 10, wherein:
the at least one oxidizing agent of the blonding powder (B) is selected from the group of sodium peroxodisulfate, potassium peroxodisulfate, sodium percarbonate, sodium peroxomonosulfate, potassium peroxomonosulfate, and mixtures of these compounds.

17. The method for brightening keratinous fibers of claim 10, wherein:
the blonding powder comprises from about 1 to about 17% by weight of the oils, including components b) and c), based on the weight of the blonding powder (B).

18. The method for brightening keratinous fibers of claim 10, wherein:
the weight ratio of the total amount of branched fatty alcohols with 8-24 carbon atoms to the total amount of dialkyl ethers with 6 to 18 carbon atoms in the alkyl group in blonding powder (B) is from about 2 to about 8.

19. The kit-of-parts according to claim 1, wherein the at least one oxidizing agent is included in the blonding powder (B) in a total amount of from about 22-45%, based on the weight of the blonding powder (B).

20. The kit-of-parts according to claim 1, wherein the at least one dialkyl ether having 6 to 18 C atoms in the alkyl group comprises dialkyl ethers with branched alkyl groups each having 6 to 18 C atoms, wherein the alkyl groups are substituted in the 2 position by an ethyl group.

* * * * *